United States Patent [19]

Bogden

[11] Patent Number: 4,610,869
[45] Date of Patent: Sep. 9, 1986

[54] METHOD FOR IN VIVO TESTING OF BIOLOGICAL RESPONSE MODIFIERS INCLUDING MONOCLONAL ANTIBODIES

[75] Inventor: Arthur E. Bogden, Westboro, Mass.
[73] Assignee: EG&G Mason Research Institute, Worchester, Mass.
[21] Appl. No.: 544,974
[22] Filed: Oct. 24, 1983
[51] Int. Cl.$^4$ ..................... A61K 49/00; A61K 49/02
[52] U.S. Cl. ........................................ 424/9; 424/1.1; 935/107; 128/630
[58] Field of Search ...................... 128/630, 653, 659; 424/1.1, 9; 935/107

[56] References Cited

PUBLICATIONS

"Comparison of the Hyman Tumor Cloning (HTC) and Subrenal Capsule (SRC) Assays," Bogden, et al., Asco Abstracts C-11, Mar., 1983.
"Cross-Resistance to Drugs of Human Tumors as Determined by Correlation Analysis of Data from the Subrenal Capsule Assay (SRCA)," Reich, et al., Asco Abstracts C-151, Mar. 1983.
"Experience with Combination and Sequential Methotrexate and 5-Fluorouracil Treatment Against Human Colorectal Cancer in the 6-Day Subrenal Capsule Assay (SRCA)," Costanza, et al., Asco Abstracts C-500, Mar., 1983.
"Response Rates of Surgical Explants of Human Tumors to Chemotherapeutic Agents in the 6-Day Subrenal Capsule Assay (SRCA)," Reich, et al., AACR Abstracts 1216, Mar. 1983.
"Activity of Phase 1 Drugs Homoharringtonine (HHT) and Tricyclic Nucleotide (TCN) Against Surgical Explants of Human Tumors in the 6-Day Subrenal Capsule (SRC) Assay," Cobb, et al., Proc. of AACR 23:222 (1982).
"Drug Sensitivity Profiles of Primary Tumors and Their Metastases: 6-Day Subrenal Capsule Assay," Bogden, et al., Proc. of ASCO 1:12 (1982).
"6-Day Subrenal Capsule Assay Results and Response to Chemotherapy of Patients with Lymphoma," Reich, et al., Proc. of ASCO 1:17 (1982).
"Clinical Update on the Subrenal Capsule Assay as a Predictive Test for Tumor Response to Chemotherapy," Griffin, et al., Proc. of ASCO 1:17 (1982).
"Stimulation of Tumor Growth by Anticancer Drugs and Hormones in the 6-Day Subrenal Capsule Assay," Reich, et al., 13th International Cancer Congress Official Abstracts (1982).
"Activity of Drugs Against Human Tumors as Determined by the 6-Day Subrenal Capsule (SRC) Assay," Reich, et al., Proc. of AACR 23:222 (1982).
"Cross-Resistance of Human Tumors as Determined by the Subrenal Capsule Assay," Reich, et al., ASCO Abstracts C-115, Mar., 1981.
"The Subrenal Capsule Assay as a Predictor of Tumor Response to Chemotherapy," Griffin, et al., ASCO Abstracts C-115, Mar., 1981.
"Surgical Explants of Human Tumors as First Transplant Generation Xenografts for New Drug Screening In Vivo," Bogden, et al., AARC Abstract, 1980.
"Reproducibility of Chemotherapy Response Profiles of Human Tumor Explants in the 6-Day Subrenal Capsule (SRC) Assay," Bogden, et al., AACR Abstract, 1981.
"Uptake of I-125 Monoclonal Antibody in Athymic Nude Mouse/Human Tumor Models," Hnatowich, et al., 1982 Abstract, Society of Nuclear Medicine 19th Annual Meeting Miami Beach, Florida, Jun. 15-18, 1982.
"Activity of Two Phase 1 Drugs, Homoharringtonine and Tricyclic Nucleotide, Against Surgical Explants of Hyman Tumors in the 6-Day Subrenal Capsule Assay," Cobb, et al., Cancer Treatment Reports, vol. 67, No. 2, Feb. 1983.
"The 6-Day Subrenal Capsule (SRC) Assay as an In Vivo Drug Testing System," Bogden, et al., 13th International Congress of Chemotherapy, 1983.
"Chemotherapy Responsiveness of Hyman Breast Tumors in the 6-Day Subrenal Capsule Assay: An Update," Bogden, et al., Breast Cancer Research and Treatment 3, 33-38 (1983).
"Activity of Two Phase I Drugs N-Methylformamide (NSC-3051) and Echinomycin (NSC-526417) Against Fresh Surgical Explants of Human Tumors in the 6-Day Subrenal Capsule (SRC) Assay," Cobb, et al., Investigational New Drugs 1, 005-009 (1983).
"An In Vivo Method for Testing Chemotherapeutic Agents Against First Transplant Generation Human Tumor Xenografts," Bogden, et al., Design of Models for Testing Cancer Therapeutic Agents, (Litton Bionetics Workshop Series No. 3), Fidler and White, eds., pp. 175-184 (1982).
"Chemotherapy Responsiveness of Human Tumors as First Transplant Generation Xenografts in the Normal Mouse: Six-Day Subrenal Capsule Assay," Bogden, et al., Cancer, vol. 48, No. 1, Jul. 1, 1981.

(List continued on next page.)

Primary Examiner—Andrew H. Metz
Assistant Examiner—Terryence Chapman
Attorney, Agent, or Firm—Finnegan, Henderson, Farabow, Garrett & Dunner

[57] ABSTRACT

In vivo method for determining the ability of biological response modifiers, including monoclonal antibodies, to interact with tumor tissue. A fresh, surgical tumor tissue specimen is implanted under the renal capsule of a host organism. A biological response modifier is administered to the host organism. The degree of interaction between the biological response modifier and the tumor tissue is determined. This method is particularly suitable for determining the ability of a biological response modifier to interact with fresh, surgically-obtained tumor tissue when using an immunocompetent host in an assay of short duration.

20 Claims, No Drawings

OTHER PUBLICATIONS

"Responsiveness of Gynecologic Tumors to Chemotherapeutic Agents in the 6-Day Subrenal Capsule Assay," Hunter, et al., Gynecologic Oncology 14, 298–206 (1982).

"In Vivo Localization of Monclonal Antibody in Fresh Surgical Explants of Human Tumors: 3-Day Subrenal Capsule (SRC) Assay," Bogden, et al., AACR Abstract, May 1983.

"A Rapid Screening Method for Testing Chemotherapeutic Agents Against Human Tumor Xenografts," Bogden, et al., Gustan Fischer, New York, Inc. Publ., 1978.

"Advances in Chemotherapy Studies with the Nude Mouse," Bogden, et al., The Nude Mouse in Experimental and Clinical Research, vol. 2, p. 367 (1982).

METHOD FOR IN VIVO TESTING OF BIOLOGICAL RESPONSE MODIFIERS INCLUDING MONOCLONAL ANTIBODIES

The Government has rights in this invention pursuant to Contract No. NO1-CM-07325 awarded by the National Cancer Institute.

BACKGROUND OF THE INVENTION

The present invention relates to a method for determining the ability of a biological response modifier (hereafter, sometimes referred to as "BRM") to interact with specific cells. More specifically, the invention relates to a method for determining the ability of a BRM to interact with a fresh, surgically-obtained tumor tissue explanted into a host organism.

"BRM" represents a term recently coined to include the many agents and approaches whose mechanisms of action involve the individual's own biological responses. Generally defined, BRM are those agents or approaches that modify the relationship between the tumor and host by modifying the host's biological response to the tumor cells with resultant therapeutic effects.

BRM may modify responses in several ways, including but not limited to, the following: (a) increasing the host's antitumor responses through augmentation and/or restoration of effector mechanisms or mediators of the host's defenses or decreasing the components of the host's reaction that may be deleterious; (b) increasing the host's defenses by the administration of natural biologics (or the synthetic derivatives thereof) as effectors or mediators of an antitumor response; (c) augmenting the host's responses to modified tumor cells or vaccines, which might stimulate a greater response by the host or increase tumor cell sensitivity to an existing response; (d) decreasing the transformation and/or increasing differentiation (maturation) of tumor cells, and (e) increasing the ability of the host to tolerate damage by cytotoxic modalities of cancer treatment. BRM also interact with neoplasm or alter a host's response to neoplasm.

BRM include, but are not limited to, immunomodulators, and/or immunostimulating agents, interferons and interferon inducers, thymosins, lymphokines and cytokines monoclonal and polyclonal antibodies, antigens, effector cells, and naturally occurring substances active during embryonic development. As used herein, monoclonal antibodies are specifically included among the class of agents referred to as BRM.

Biological response modifiers are an increasingly important component in the methodologies used to treat tumors. A BRM may also serve as a localizing device to identify and localize tumors and/or metastases, or as a therapeutic agent either alone or as a carrier for a tumor-attacking substance.

Certain characteristics of monoclonal antibodies have hampered their overall usefulness in tumor treatments. In particular, the high degree of specificity of monoclonal antibodies and the inherent heterogeneity of the cell populations comprising solid neoplasma necessitates predetermining, for each patient, specific antigen expression as well as availability in an in vivo solid tumor milieu.

All cells, including tumor tissues, have sites on their outer membranes known as antigens and receptors. Antigens and receptors are very specific molecules. The types of antigens and receptors present control which BRM is capable of attaching and altering the nature of the cell's activities. Cells from the same type of tumor, but originating in different organisms, may possess different antigens and receptors.

Previous methods of identifying the specific BRM capable of attaching to the particular cell wall via an antigenic or receptor site, and thereby altering the cell's activity, are often time consuming and expensive. These procedures basically involve the removal and growth of tumor tissue. The tumor tissue may be grown in vitro or in vivo. If the tumor tissue is to be propagated in vivo, it is grown subcutaneously in athymic mice. Generally, several generations of tumor tissue growth are required either in vitro or in vivo to establish a stabilized cell line which can then be tested for antigen presence. The establishment of such a cell line can take as long as one to two years.

Disadvantageously, the cost of in vitro growth of tumor tissue is greater than in vivo. Also, in an in vitro system, it is impossible to determine whether the BRM being tested would actually be able to reach an in vivo tumor tissue because an in vitro test cannot evaluate factors such as tissue permeability or coupling factors of the BRM, the ability of a BRM to travel unaltered through an organism to the tumor tissue, and host-mediated detoxification factors that could affect the effectiveness of the BRM.

In response to these drawbacks of in vitro testing, in vivo systems were developed. However, the prior art in vivo systems possess a unique set of disadvantages.

In particular, the in vivo systems of the prior art require the use of an athymic or thymectimized host because of a belief that an immunocompromised host is necessary to avoid a host-mediated reaction to the implanted tumor tissue in an assay that takes six days or more. In addition, tumor tissue is either established first in an in vitro culture or is serially passaged subcutaneously in vivo to stabilize it to a degree sufficient to support growth in a host. Additionally, no prior art in vivo system works in less than six days.

SUMMARY OF THE INVENTION

The present invention overcomes the problems of the prior art by providing an in vivo method for determining the ability of a BRM to interact with tumor tissue cells which utilizes implantation into an animal host of fresh, surgically-obtained tumor tissue. The present invention also allows for the use of both immunocompetent hosts and immunocompromised hosts. Advantageously, the use of immunocompetent hosts costs considerably less than immunocompromised hosts. Also advantageously, the method of the present invention may be accomplished in only a three-day testing period. The inventor has found that such a three-day test may be accomplished, even in an immunocompetent host, without experiencing the artifacts of host-mediated response to the tumor tissue that would preclude usefulness of the assay.

Additional objects and advantages of the invention will be set forth in part in the description which follows, and in part will be obvious from the description or may be learned by practice of the invention. The objects and advantages of the invention may be realized and attained by means of the instrumentalities and combinations particularly pointed out in the appended claims.

To achieve the objects and in accordance with the purpose of the invention, as embodied and broadly described herein, a method for determining the ability of a biological response modifier to interact with tissue cells comprises: (a) implanting fresh, surgically-obtained tumor tissue under the renal capsule of a host organism; (b) administering a biological response modifier to the host organism; and (c) determining the degree of interaction between the biological response modifier and the tumor tissue.

The method also comprises: (a) administering the biological response modifier to the host organism; (b) implanting fresh, surgically-obtained tumor tissue under the renal capsule of a host organism; and (c) determining the degree of interaction between the biological response modifier and the tumor tissue.

The present invention may also be used to screen a battery of BRM to determine the BRM best suited for use in treatment of a tumor bearing patient. When used for this purpose, the method of the present invention comprises: (a) implanting pieces of fresh tumor tissue of the same type, surgically-obtained from a patient, under the renal capsules of a plurality of host organisms; (b) administering a different biological response modifier to each host organism; and (c) determining which biological response modifier exhibits the greatest response to or specificity for the tumor tissue.

Additionally, the present invention may be used to predict the clinical usefulness of a BRM to a type of tumor. Such a prediction is done in a pre-clinical screening of potential BRMs and comprises: (a) surgically obtaining, from a plurality of patients, fresh pieces of tumor tissue of the same type; (b) implanting, under the renal capsule of a plurality of host organisms, the pieces of fresh tumor tissue; (c) administering the same biological response modifier to each of the plurality of host organisms; and (d) determining the response rate or number of host organisms exhibiting the greatest response to the biological response modifier or greatest interaction between the biological response modifier and the tumor tissue.

DETAILED DESCRIPTION OF THE PREFERRED EMBODIMENTS

Reference will now be made in detail to the presently preferred embodiments of the invention. In accordance with the invention, a method for determining the ability of a biological response modifier to interact with tissue cells comprises: (a) implanting fresh, surgically-obtained tumor tissue under the renal capsule of a host organism; (b) administering a biological response modifier to the host organism; and (c) determining the degree of interaction between the biological response modifier and the tumor tissue.

A "biological response modifier", as defined above, may be capable of inducing a host response that interferes with the activity of tumor tissue. The term "biological response modifier" specifically includes substances known as monoclonal antibodies. Biological response modifiers also include, but are not limited to, compounds such as polyclonal antibodies, vitamins and their precursors, interferons and naturally occurring substances capable of reacting with neoplasm and capable of altering host cellular responses. Biological response modifiers do not include substances classified as chemotherapeutic drugs. Chemotherapeutic drugs include, but are not limited to, cytotoxic agents such as cytoxin, adriamycin and 5-fluorouracil.

Representative vitamins include precursors and derivatives of vitamin A. Representative interferons include alpha, beta, and gamma interferons. An example of a naturally occurring substance capable of altering cellular response is Mullerian Inhibition Substance (MIS). Representative polyclonal and monoclonal antibodies intended for use in the present invention include, but are not limited to, anti-CEA (carcinoembryonic antigen) and anti-PAP (prostatic acid phosphatase).

A monoclonal antibody (hereinafter "MAb") interacts with antigens, structures present on the outer surface of the cells. Different antigens may be present on different cells. Due to the high degree of specificity which MAbs exhibit for certain antigens, it is necessary to determine whether an antigen which would serve to attract a particular MAb is present on the cells in tumor tissue. The present invention provides a method for this purpose.

Other BRM, for example interferon, may also react with cell surfaces. Some BRM, for example MAb-toxin conjugates, are taken into or incorporated into the cell. Still other BRM stimulate the host immune system, or stimulate or mediate host cellular or humoral response to induce a host-mediated reaction with the tumor tissue.

Tumor tissue to be tested is obtained from a patient by surgical biopsy methods. Only an amount sufficient to demonstrate BRM activity is necessary. Preferably, a piece of tumor about 1 $mm^3$ per animal is used. The tumor tissue is preferably maintained in a buffered culture solution from the time between removal and implantation into a host. Preferably, the culture solution contains an antibiotic. It is also preferred that the time period between removal and implantation is not more than about 48 hours, most preferably about 3 to about 4 hours.

A host animal is chosen as the implant recipient. Preferably, the host is chosen from the group of animals that include, but are not limited to, rodents. Most preferably, the host is a mouse.

The tumor tissue must be implanted into an area of the host capable of supporting tissue viability. The subcapsular site of the kidney, providing a rich, vascularized bed for maintenance and growth of the tumor tissue, is the preferred site for implantation of the tumor tissue. The small size of the tumor tissue which is implanted, in combination with the ability of the subrenal capsule site to supply the nutrients necessary to maintain viability of the tissue, ensures that necrosis of portions of the implanted tumor will not occur within a 3 to 4 day test period. Otherwise, BRM may nonspecifically localize in the necrosed tissue, simulating an interaction between the viable tumor tissue and the BRM, a reaction which will be counterfeit if the viable tumor tissue lacks the necessary antigenic characteristics for interaction with the administered BRM.

The method for implantation of the tumor tissue under the subrenal capsule is detailed in "A Rapid Screening Method for Testing Chemotherapeutic Agents Against Human Xenografts" Bogden, A.E. et al., Proceedings of the Symposium on the Use of Athymic (Nude) Mice in Cancer Research. Houchens, D.P. et al, eds. 1978; Gustav Fisher, Inc., New York, pp. 231-250. Briefly, the kidney is exteriorized and a small incision is made in the renal capsule of the host organism. The tumor tissue is slipped under the capsule and rests upon the parenchyma of the kidney. The implanted tissue may be measured in situ, using magnification, if it is predicted that reaction with the BRM to be administered will cause a change in tumor size. The kidney is then reinserted into the peritoneal cavity. The incisions in the peritoneum and skin are closed. It is preferred that the incision in the renal capsule not be surgically closed, as this procedure may tend to traumatize the kidney tissue, thereby increasing the chance of a recognizable artifact occurring.

There are additional factors that cause recognizable artifacts in the assay. Sterile procedures must be followed during xenograft implantation, as contamination with ubiquitous nonpathogens can result in marked cellular infiltration in or around the implant. Excessive traumatization at the implant site can also cause excessive cellular infiltration.

When using immunocompetent host organisms, the time period necessary for establishment of the tumor tissue in the host organism is generally not more than one day. If an excessive amount of time is allowed for establishment of the tumor tissue in immunocompetent host organisms, a host-mediated response could be mounted against the tumor tissue, interfering with interaction between the BRM and the tumor tissue antigens.

If athymic or thymectimized host animals are utilized, the duration of the time period used to establish tumor tissue in the subrenal capsule is not as critical. However, since one of the advantages of the present invention is determination of interaction between the BRM and the tumor tissue in a shortened time period, e.g. three days, it is not preferable a prolong the time for tumor tissue establishment.

In an embodiment of the present invention, it is necessary to administer the BRM prior to implantation of the tumor tissue into the host. Such a procedure is hereinafter referred to as "preconditioning". Preconditioning is used when the BRM to be tested is one that causes the host animal to mount a cellular or humoral response which takes longer than about three days to initiate. Examples of BRM which are best used in a preconditioning step include, but are not limited to, vaccines and substances such as interleukin.

In another embodiment of the present invention, the BRM is administered after the tumor implantation, preferably after the time period allowed for tumor tissue establishment. In this embodiment, upon completion of the implantation of the tumor tissue, a time period sufficient to allow the tumor tissue to establish itself in the subcapsular site is allowed before administration of the BRM. Preferably, this time ranges from about one to about three days.

The method of administration for either embodiment is preferably that which would be suitable for use and treatment of the patient in whom the tumor originated. As such, suitable methods of administration include, but are not limited to, intravenous, oral, intraperitoneal, or intramuscular modes of administration.

In either embodiment, after the tumor tissue is established, a length of time, if necessary, sufficient for interaction between the BRM and the tumor tissue implanted in the subrenal capsule of the host organism is allowed. Such a time may range from 6 hours to 5 days, depending in part upon the particular BRM administered. Preferably 6 to 48 hours are sufficient to allow interaction between the BRM and the host organism.

When immunocompetent host organisms are utilized in the method of the present invention, preferably not more than 6 days are allowed for interaction following tumor implantation due to the possibility of a host-mediated response against the tumor tissue which would create a counterfeit result.

The method of the present invention may thus be accomplished within three days from implantation of the tumor. The three day time span is preferable, especially when using immunocompetent hosts.

Dosages used when administering the biological response modifier to the host animal are calculated on a weight or unit of substance administered/weight of host organism ratio, designed, if so desired, to correspond to the desired dosage in the patient. The optimal methods of administration and dosages will vary depending on the particular characteristics of the BRM. Dosages and methods of administration, including those set forth above, can be readily ascertained without undue experimentation by those of ordinary skill in the art.

At the end of the time period allowed for interaction, the tumor tissue is examined to determine the degree of interaction between the BRM and the tumor tissue. This interaction may be determined either while the tumor tissue remains in the host organism or after the tumor tissue has been removed from the host organism. The choice of examination before or after removal of the tissue depends upon the method of examination chosen.

Methods of examination contemplated for use in the present invention include, but are not limited to, histological examination or quantitative determinations, such as examination for radioactivity, examination for fluorescent activity, or assay for chemical presence. The selection of a particular technique is dependent upon the type of biological response modifier administered and presents no problem to an ordinarily skilled artisan. If a quantitative determination using examination for radioactivity or fluorescence is contemplated, it is necessary that a radioactive nuclide or a fluorescent marker be incorporated into or attached to the BRM prior to administration of the BRM to the host animal. Such incorporation can be achieved by means well-known in the art.

One method of examining for the presence of attached BRM in the tumor tissue is to screen for radioactivity. In this method, before administration of the BRM to the host, a suitable radioisotope or radionuclide is attached to the BRM. The radioactive tag preferred for use with the present invention is capable of being scanned using known methods and is also nonfatal to the host organism when present internally for a period of about 3 to 7 days. Preferably, such radioisotopes include, but are not limited to, radioisotopes of carbon, iodine, phosphorous, and hydrogen and radionuclides such as Indium-111. Additionally, it is possible to alter the molecular composition of a BRM to include a radioisotope within the BRM. If such a system is employed, it is desirable to choose a radioisotope such that the modified molecule is similar in molecular weight to the original BRM molecule.

Imaging, for example, for radioactive biological response modifiers may be done when the tumor tissue is still located under the renal capsule of the host animal. Such scanning would, if the BRM has attached to the tumor tissue, show a concentration of radioactivity in the tumor tissue area of the subrenal capsule.

Another way of examining for interaction between the BRM and the tumor tissue is by scanning for fluorescent activity. If this technique is chosen, a fluorescent material is attached to the BRM before administration of the BRM to the host organism. Any known method of attaching fluorescent compounds to biologically active compounds is contemplated for use in the present invention.

It is also possible to remove the tumor tissue from under the renal capsule and quantitatively measure the amount of BRM attached to the tumor tissue. In such a situation, the amount of radio-labelled or fluorescent-labelled BRM actually attached to the tumor tissue could be determined by a comparison between the amount of radioactivity or fluorescence located in the tumor tissue and the total amount of radioactivity or fluorescence originally administered to the host animal.

Chemical assays and immunological assays are additional methods of determining the extent of the attachment of the BRM to the tumor tissue. In these methods, the tumor tissue is excised from the renal capsule of the host animal and is assayed in a manner which will indicate the presence of the particular BRM administered. These methods would also be quantifiable by traditional histochemical and quantitative or biochemical analysis methods and as such would serve to indicate the amount of BRM capable of attaching to the implanted amount of tumor tissue.

The present invention has numerous uses both in the detection and treatment of tumor tissues. The inventive method identifies BRM which are useful as a localization method for locating both primary tumor sources and metastases. Either radioactive or fluorescent-imaging techniques would serve to identify the site of primary tumors and metastases. This is particularly useful in situations where the primary tumor site is not identifiable by conventional radiographic or other diagnostic means. In addition, minute metastases, known as micrometastases, would become visible in situations where they have not been known to exist.

A radioactive-labelled BRM would selectively irradiate tumor tissue in situ, allowing for levels of radioactivity not suitable if nonselectively directed towards the entire patient. A BRM may also be used as a carrier for chemotherapeutic agents. It would then be possible to concentrate the effect of a chemotherapeutic agent in the tumor tissue and allow use of concentrations of chemotherapeutic agents previously ineffective due to the overall destructive effect on a patient.

Other substances useful when conjugated with a BRM are cellular toxins. Examples of cellular toxins include, but are not limited to, diptheria toxin and ricin. A preferred toxin would be one of sufficient toxicity to cause a fatal reaction in tumor cells in a very small dosage. The invention enables administration of BRM-conjugated toxin to destroy tumor tissue without allowing interaction between the toxin and normal tissues.

The present invention also indentifies the MAb of choice for use as a carrier for a cellular toxin. When the MAb of choice is used as a carrier, the ability of the cellular toxin to permeate the cell membrane is increased.

The invention is also useful in determining the potential relative effectiveness of a variety of BRM when used against a particular tumor tissue. This method aids a physician in determining whether a particular BRM should be used in therapy for a patient. A BRM so identified may be used as a therapeutic agent itself or may be used as a tag or carrier to deliver therapeutic agents to the tumor site. The BRM, such as a MAb, may serve as a carrier for a variety of therapeutic agents, including radioactive materials, chemotherapeutic agents, and cellular toxins.

In this embodiment, the invention may be used to screen a battery of BRM to determine the BRM best suited for use in treatment of a patient's tumor. When used for this purpose, the method of the present invention comprises: (a) implanting pieces of fresh tumor tissue of the same type, surgically-obtained from a patient, under the renal capsules of a plurality of host organisms; (b) administering a different biological response modifier to each host organism; and (c) determining which biological response modifier exhibits the greatest response to or specificity for the tumor tissue.

Additionally, the present invention may be used to predict the clinical usefulness of a BRM to a specific type of tumor. Such a prediction is done in a pre-clinical screening of potential BRM and comprises: (a) surgically obtaining, from a plurality of patients, fresh pieces of tumor tissue of the same type; (b) implanting, under the renal capsule of a plurality of host organisms, pieces of fresh tumor tissue; (c) administering the same biological response modifier to each of the plurality of host organisms; and (d) determining the response rate or number of host organisms exhibiting the greatest response to the biological response modifier or greatest interaction between the biological response modifier and the tumor.

The following examples are designed to elucidate the teachings of the present invention, and in no way limit the scope of the invention. Various other modifications and equivalents of the examples will readily suggest themselves to those of ordinary skill in the art, particularly after the issuance of this patent, without departing from the spirit or scope of the present invention.

EXAMPLE 1

In vivo localization of 111-indium-labelled monoclonal carcinoembryonic antigen (CEA) antibody (C-19, specific activity 0.2–0.3 $\mu Cu/\mu g$) in fresh, surgical explants of human colon tumors was determined. Tumor fragments were implanted under the renal capsules of normal, immunocompetent CDF-1 mice, obtained from Animal Genetics and Production Section of the National Cancer Institute, Bethesda, Md., on day 0, using the method of Bogden, et al., The Nude Mouse in Experimental and Clinical Research Vol. 2 (Fogh, J. and Giovanella, B. C., eds.) New York: Academic Press, Inc., 1982. On day 2, 10 $\mu g$ of labelled antibody was administered by the intraveneous route. On day 3, radioactivity, as a percent injected dose per gram of tumor, was determined. Similarly labelled monoclonal anti-PAP (prostatic acid phosphatase) antibody was used as control serum. Two of five colon tumors showed marked localization of specific antibody as indicated by anti-CEA/anti-PAP ratios of 14 and 23.

EXAMPLE 2

This example illustrates the use of the method of the present invention for determining the sensitivity (responsiveness) of fresh surgical explants of human tumors to gamma interferon ($\gamma$-IFN).

On day 0, groups of normal $CDF_1$ mice were implanted subcapsularly with 1 $mm^3$ fragments of fresh surgical specimens obtained from a human lung tumor and a lymphoma. Animals were obtained from the Animal Genetics and Production Branch, Division of Cancer Treatment, National Cancer Institute, and tumor tissue was donated by local hospitals. The method and sites of tumor xenograft implantation were those described by Bogden, et al., Proceedings of the Symposium on the Use of Athymic (Nude) Mice in Cancer Research (Houchens, D. P. et al. eds.) New York: Gustav Fischer, INc., 1978. On days 1 and 2, $\gamma$-IFN was administered intramuscularly, twice daily, at a dose of $5 \times 10^6$ units/Kg. In each assay, two groups were administered only 65 -IFN. γ-IFN was obtained from Hoffman-LaRoche. On day 3, one hour prior to sacrifice, one control group and one γ-IFN treated group were injected intravenously with tritiated leucine at 35 μC/animal. The other two groups were injected in a similar manner with tritiated thymidine at 35 μC/animal. After one hour, tunors were enucleated, weighed on an electrobalance, and the amount of radioactivity incorporated into the tumor tissue was determined by oxidation and counting in a liquid scintillation spectrometer. The incorporated radiation was reported as counts per minute per gram of tissue (cpm/gm).

In the lymphoma, protein synthesis, as indicated by $^3$H Leucine uptake in the tumor, was decreased 40% in the γ-IFN treated group as compared to the control. DNA synthesis, as indicated by $^3$H Thymidine uptake in the tumor, was decreased 77% in the γ-IFN treated group as compared to the control.

In the lung tumor, protein synthesis was not decreased by γ-IFN treatment and DNA synthesis was decreased by only 40%.

It will be apparent to those skilled in the art that various modifications and variations can be made in the method of the present invention without departing from the scope or spirit of the invention. Thus, it is intended that the claims cover the modifications and variations of the invention.

What is claimed is:

1. A method for determining the ability of a biological response modifier to interact with tissue cells comprising:
   a. implanting fresh, surgically-obtained tumor tissue under the renal capsule of a host organism;
   b. administering said biological response modifier to said host organism; and
   c. determining the degree of interaction between said biological response modifier and said tumor tissue.

2. The method of claim 1 wherein said biological response modifier is a monoclonal antibody.

3. The method of claim 1 wherein said biological response modifier is a polyclonal antibody.

4. The method of claim 1 wherein said biological response modifier is a vitamin derivative or precursor.

5. The method of claim 1 wherein said biological response modifier is an interferon.

6. The method of claim 1 wherein said biological response modifier is a naturally-occurring substance.

7. The method of claim 6 wherein said naturally-occurring substance is interleukin.

8. The method of claim 1 wherein the host is a rodent.

9. The method of claim 8 wherein the host is immunocompetent.

10. The method of claim 8 wherein the host posesses no thymus gland.

11. The method of claim 1 wherein said biological response modifier is radiolabelled.

12. The method of claim 11 wherein said determining is accomplished by radioactive imaging.

13. The method of claim 12 wherein said imaging is accomplished while said tumor tissue is located within said host.

14. The method of claim 12 wherein said imaging is accomplished after said tumor tissue is removed from said host.

15. The method of claim 1 wherein said biological response modifier is labelled with a fluorescent substance.

16. The method of claim 15 wherein said determining is conducted by fluorescent imaging.

17. The method of claim 1 wherein said determining is conducted by a chemical assay.

18. A method for screening a plurality of biological response modifiers to identify the biological response modifiers best suited for treatment of a tumor comprising:
   a. implanting pieces of fresh tumor tissue of the same type, surgically-obtained from a patient, under the renal capsule of a plurality of host organisms;
   b. administering a different biological response modifier to each host organism; and
   c. determining which biological response modifier exhibits the greatest response to or interaction with the tumor tissue.

19. A method for predicting the clinical usefulness of a biological response modifier comprising:
   a. surgically obtaining, from a plurality of patients, fresh pieces of tumor tissue of the same type;
   b. implanting, under the renal capsule of a plurality of host organisms, said pieces of fresh tumor tissue;
   c. administering the same biological response modifier to each of the plurality of host organisms; and
   d. determining which host organism exhibits the greatest response to said biological response modifier or greatest interaction between said biological response modifier and said tumor tissue.

20. A method for determining the ability of a biological response modifier to interact with tissue cells comprising:
   a. administering said biological response modifier to said host organism;
   b. implanting fresh, surgically-obtained tumor tissue under the renal capsule of a host organism; and
   c. determining the degree of interaction between said biological response modifier and said tumor tissue.

* * * * *